United States Patent
Frigg

(10) Patent No.: US 9,161,821 B2
(45) Date of Patent: Oct. 20, 2015

(54) ADVANCED BONE MARKER AND CUSTOM IMPLANTS

(75) Inventor: Robert Frigg, Langendorf (CH)

(73) Assignee: DEPUY SYNTHES PRODUCTS, INC., Raynham, MA (US)

(*) Notice: Subject to any disclaimer, the term of this patent is extended or adjusted under 35 U.S.C. 154(b) by 265 days.

(21) Appl. No.: 13/156,703

(22) Filed: Jun. 9, 2011

(65) Prior Publication Data

US 2012/0010710 A1 Jan. 12, 2012

Related U.S. Application Data

(60) Provisional application No. 61/362,456, filed on Jul. 8, 2010.

(51) Int. Cl.
| | |
|---|---|
| A61B 19/00 | (2006.01) |
| A61B 17/15 | (2006.01) |
| A61B 17/80 | (2006.01) |
| A61B 17/56 | (2006.01) |

(52) U.S. Cl.
CPC ............ *A61B 19/5244* (2013.01); *A61B 19/50* (2013.01); *A61B 17/15* (2013.01); *A61B 17/80* (2013.01); *A61B 2017/568* (2013.01); *A61B 2019/501* (2013.01); *A61B 2019/502* (2013.01)

(58) Field of Classification Search
CPC ...... A61B 17/15; A61B 17/155; A61B 17/80; A61B 17/8061; A61B 19/5244; A61B 19/50
See application file for complete search history.

(56) References Cited

U.S. PATENT DOCUMENTS

| | | | |
|---|---|---|---|
| 8,934,961 B2 | 1/2015 | Lakin et al. | |
| 2002/0107522 A1 | 8/2002 | Picard et al. | |
| 2002/0147451 A1* | 10/2002 | McGee | 606/62 |
| 2005/0197814 A1 | 9/2005 | Aram et al. | |
| 2008/0077158 A1 | 3/2008 | Haider et al. | |
| 2008/0319448 A1 | 12/2008 | Lavallee et al. | |
| 2011/0029093 A1* | 2/2011 | Bojarski et al. | 623/20.35 |
| 2011/0130761 A1* | 6/2011 | Plaskos et al. | 606/87 |

FOREIGN PATENT DOCUMENTS

WO 2009/076758 6/2009

* cited by examiner

*Primary Examiner* — Jason-Dennis Stewart
(74) *Attorney, Agent, or Firm* — Fay Kaplun & Marcin, LLP

(57) ABSTRACT

A method for replacing a portion of a target bone in a living body includes the steps of attaching one or more first markers to a target bone, establishing a medical three-dimensional representation of the target bone, performing a virtual resection of a resection portion, the virtual resection constructing a three-dimensional representation of the resection portion and a three-dimensional representation of the remaining target bone including cutting edges, providing a virtual pattern of the resection portion, obtaining an implant or graft portion for replacing the resection portion of the target bone by using the virtual pattern of the resection portion, resecting the resection portion from the target bone according to the virtual resection using the first reference system of coordinates and coupling the implant or graft portion to the target bone in a position substantially matching a position of the resection portion before the actual resection.

9 Claims, 8 Drawing Sheets

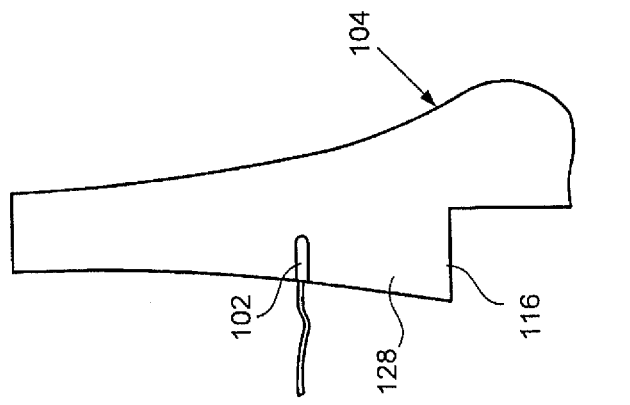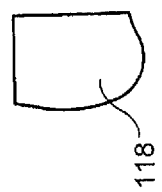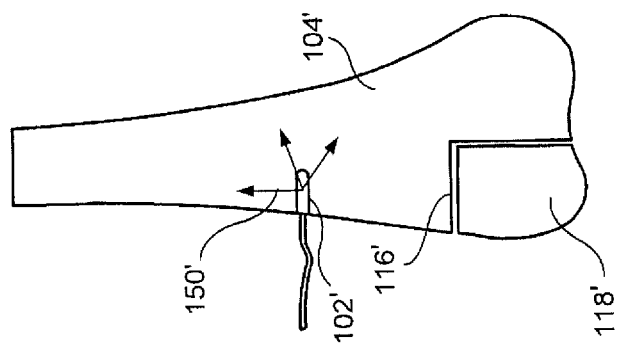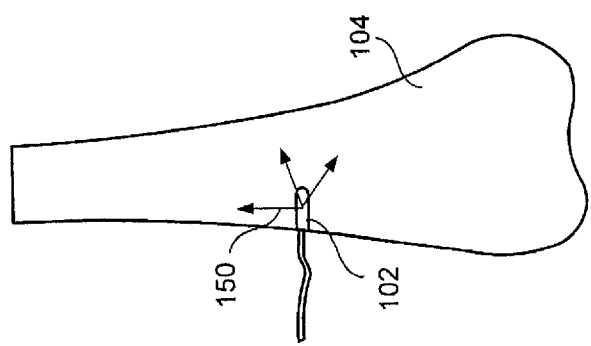

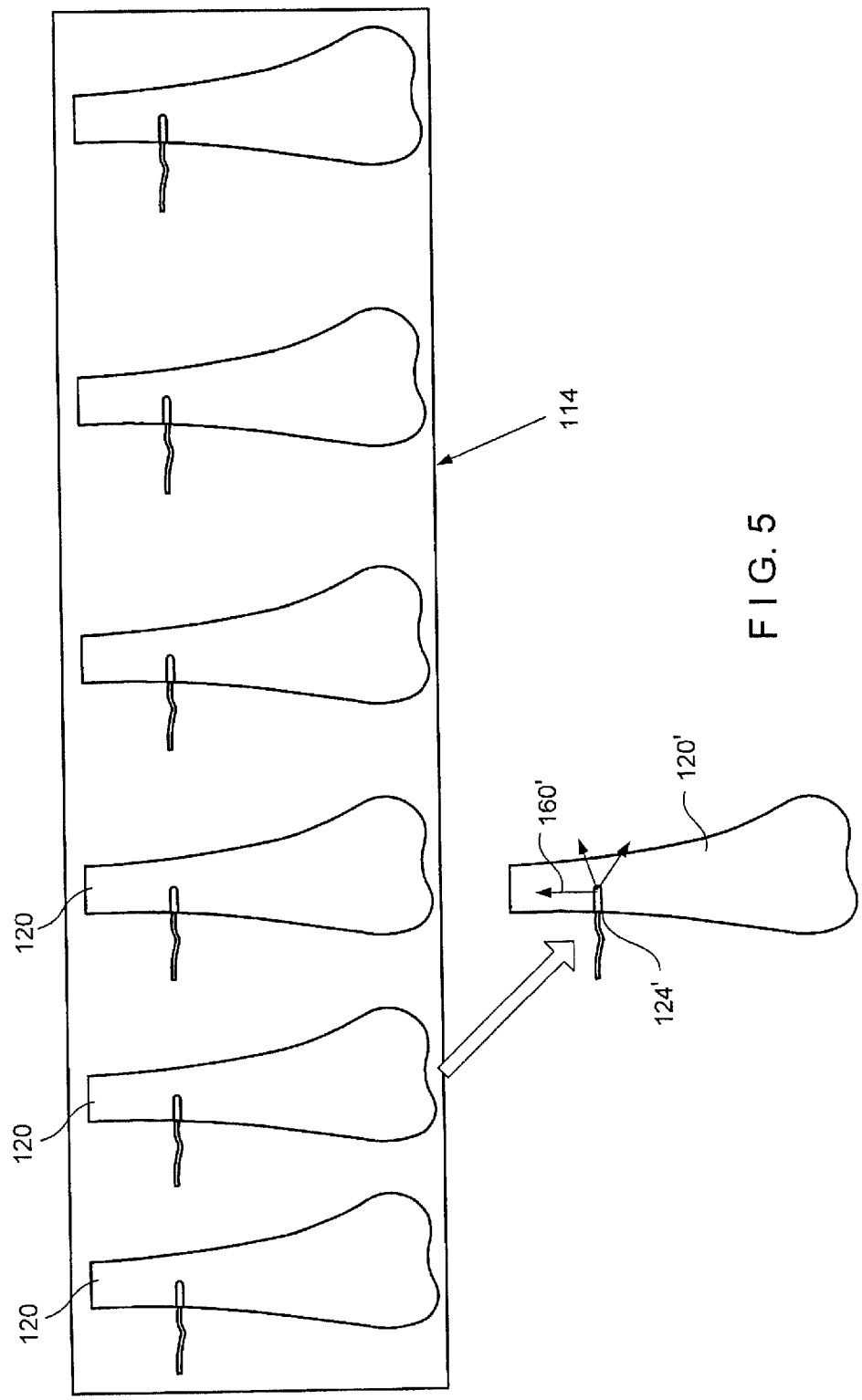

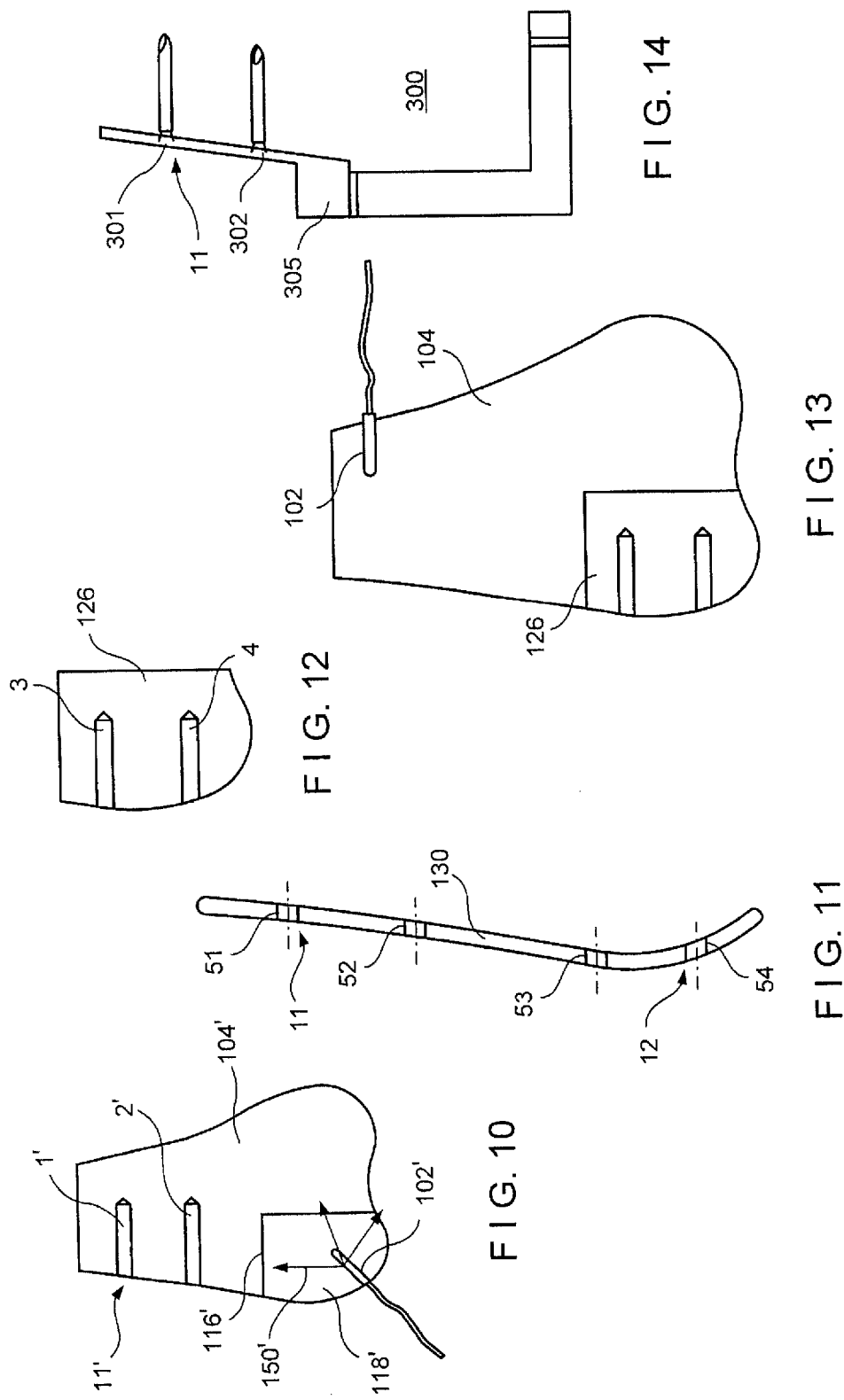

ADVANCED BONE MARKER AND CUSTOM IMPLANTS

PRIORITY CLAIM

The present application claims priority to U.S. Provisional Application Ser. No. 61/362,456 filed on Jul. 8, 2010 and entitled "Advanced Bone Marker and Custom Implants," the entire disclosure of which is incorporated herein by reference.

FIELD OF THE INVENTION

The present invention relates to the treatment of fractures including the use of markers in implant or bone graft procedures and, in particular, to the use of one or more bone markers to accurately perform a virtual resection permitting an optimally suited replacement portion of bone to be selected, sized and shaped for precise fit with the edges of the cavity left by the resected portion of bone.

BACKGROUND

Bone grafting is a surgical procedure that replaces missing bone with an artificial, natural or synthetic substitute. Bone grafting may be used to repair fractures that are complex, pose a significant health risk to the patient or which fail to heal properly. A damaged or fractured portion of the bone may be removed and replaced with a substitute sized and shaped to correspond with the removed portion of the bone. However, properly fitting the replacement bone to match the resected portion is very difficult and time consuming. A surgeon or other health professional visually adjusts by, for example, filing down the replacement bone to match the resected portion of the bone as closely as possible. Visual adjustments, however, are inevitably often unreliable and inaccurate.

SUMMARY OF THE INVENTION

The present invention relates to a system and method for replacing a portion of a target bone in a living body, comprising the steps of attaching one or more first markers to a target bone in a desired position relative to a resection portion of the target bone to be replaced and performing a virtual resection of the resection portion using a three-dimensional representation of the target bone and a three-dimensional first reference system of coordinates defined by the one or more first markers as a reference, the virtual resection constructing a three-dimensional representation of the resection portion and a three-dimensional representation of the remaining target bone including cutting edges. Subsequently, a virtual pattern of the resection portion is provided by which an implant or graft portion for replacing the resection portion is obtained and a resection of the target bone is performed. Finally, the implant or graft portion is coupled to the target bone.

In an exemplary embodiment of the present invention, the three-dimensional representation of the resection portion previously constructed is used as the virtual pattern of the resection portion. If the resection portion of the target bone is not defective, but, for example, is affected by osteoporosis, the three-dimensional representation of the patient's own target bone may be used to provide a virtual pattern for producing an implant or graft portion.

In a further exemplary embodiment, the step of providing a virtual pattern of the resection section is performed by:
obtaining a mirrored three-dimensional representation of the patient's contralateral bone (i.e., the contralateral to the target bone) if this bone is healthy and otherwise suitable in relevant aspects wherein the three-dimensional representation of the patient's contralateral bone either comprises one or more previously attached second markers which define a three-dimensional second reference system of coordinates or the one or more second markers are virtually positioned in the three-dimensional representation of the patient's contralateral bone;
registering the mirrored three-dimensional representation of the patient's contralateral bone and the three-dimensional representation of the most suitable virtual bone; and
transferring the cutting edges at the three-dimensional representation of the remaining target bone from the first reference system of coordinates to the second reference system of coordinates.

In another exemplary embodiment, the step of providing a virtual pattern of the resection section is performed by
d1) selecting a three-dimensional representation of a most suitable virtual bone from a plurality of virtual bones provided in a digital medical library, wherein the three-dimensional representation of the most suitable virtual bone most closely matches the three-dimensional representation of the target bone and wherein the three-dimensional representation of the most suitable virtual bone either comprises one or more previously attached second markers which define a three-dimensional second reference system of coordinates or the one or more second markers are virtually positioned in the selected three-dimensional representation of the most suitable virtual bone;
d2) registering the three-dimensional representation of the target bone and the three-dimensional representation of the most suitable virtual bone; and
d3) transferring the cutting edges at the three-dimensional representation of the remaining target bone from the first reference system of coordinates to the second reference system of coordinates.

In again a further exemplary embodiment, the three-dimensional representation of the most suitable virtual bone is a three-dimensional representation of a most suitable donor bone which is selected from a plurality of donor bones comprised in a digital medical library. The most suitable donor bone is selected by comparing the three-dimensional shape of a selection of donor bones with the medical representation of the target bone.

In yet a further exemplary embodiment, the step of obtaining a graft portion is performed by resecting a graft portion from the most suitable donor bone by using the cutting edges transferred to the second reference system of coordinates defined by the one or more second markers.

In another exemplary embodiment, the step of obtaining an implant is performed by manufacturing the implant using the three-dimensional representation of the most suitable virtual bone as a pattern. The control of a manufacturing apparatus may be affected by using the second set of digital data including the second reference system of coordinates. Either a three-dimensional representation of a most suitable virtual bone comprised in a bone database or a three-dimensional representation of the mirrored contralateral bone may be defined using the second set of digital data. Suitable manufacturing methods are rapid prototyping (lithographic layer production, e.g. stereolithography, selective laser sintering, fused deposition modeling) or injection molding.

In another exemplary embodiment, the method further comprises, before the step of obtaining an implant or graft portion, the step of providing a bone plate. The bone plate includes a proximal configuration of at least two plate holes to be fixed to the remaining target bone and a distal configuration of at least two plate holes to be fixed to the implant or graft portion.

In a further exemplary embodiment, the method additionally comprises, before the step of obtaining an implant or graft portion, the step of positioning a three-dimensional representation of the bone plate in a desired position on the three-dimensional representation of the target bone during the surgical planning procedure.

In yet another exemplary embodiment, the method additionally comprises the step of virtually positioning the proximal configuration of at least two proximal bore holes in the three-dimensional representation of the remaining target bone during the surgical planning procedure. The proximal configuration then consists of at least two bore holes in a known position relative to each other and each in a known position relative to the first reference system of coordinates defined by the one or more first markers.

In again another exemplary embodiment, the method further comprises the step of virtually positioning the distal configuration of at least two distal bore holes in the three-dimensional representation of the most suitable virtual bone. The distal configuration consists of at least two distal bore holes in a known position relative to each other and each in a known position relative to the second reference system of coordinates defined by the one or more second markers.

In a further exemplary embodiment, the at least two proximal bore holes of the proximal configuration are drilled into the remaining target bone in positions coinciding with the positions of the virtually positioned proximal configuration of the at least two proximal bore holes by using the first reference system of coordinates defined by the one or more first markers as a reference. If the one or more first markers are positioned in the resection portion of the target bone the at least two bore holes of the proximal configuration are drilled before resecting the resection portion.

In another exemplary embodiment, the at least two distal bore holes of the distal configuration are drilled into the most suitable donor bone in positions coinciding with the positions of the virtually positioned distal configuration of at least two distal bore holes by using the second reference system of coordinates.

In yet another exemplary embodiment, the at least two distal bore holes of the distal configuration are produced during forming the implant by using the second reference system of coordinates.

Still another exemplary embodiment, the method further comprises the step of attaching the implant or graft portion to the bone plate by means of inserting bone fixation elements through the at least two distal plate holes into the at least two distal bore holes in the implant or graft portion.

In again another exemplary embodiment, the method further comprises the step of aligning the implant or graft portion to the remaining target bone by inserting bone fixation elements through the at least two proximal plate holes into the at least two proximal bore holes in the remaining target bone. By this means the advantage can be achieved that only the step of drilling the proximal set of at least two proximal bore holes into the remaining target bone requires a surgical navigation device.

In a further exemplary embodiment, the method additionally comprises the step of using a saw guide including a fixation portion with a proximal configuration of at least two fixation holes identical to the virtually positioned proximal configuration of at least two proximal bore holes and a guide portion including guiding means for a surgical saw along the cutting edges defined during the surgical planning procedure.

In another exemplary embodiment, the one or more second markers are only virtually positioned in the most suitable virtual bone before registering the three-dimensional representation of the target bone and the three-dimensional representation of the most suitable virtual bone.

According to one exemplary embodiment of the present invention, a system comprises:
A) a three-dimensional representation of the target bone including a three-dimensional first reference system of coordinates defined by one or more first markers attached to the target bone;
B) a digital medical library or a digital connection thereto, the digital medical library comprising a bone database with a plurality of virtual bones; and
C) a control module suitable to process the three-dimensional representation of the target bone and including a display and a user interface, wherein
D) a three-dimensional representation of each of the suitable bones comprised in the digital medical library can be imported into the control module and processed during a surgical planning procedure.

In an exemplary embodiment, the system further comprises a saw guide including a fixation portion with a proximal configuration of at least two fixation holes and a guide portion including guiding means for a surgical saw along the cutting edges defined during the surgical planning procedure.

In a further exemplary embodiment, the system additionally comprises a bone plate including a proximal configuration of at least two plate holes to be fixed to the remaining target bone and a distal configuration of at least two plate holes to be fixed to the implant or graft portion.

BRIEF DESCRIPTION OF THE DRAWINGS

Several embodiments of the invention will be described in the following by way of example and with reference to the accompanying drawings in which:

FIG. 3 illustrates a side view of an end of a target bone including a marker attached thereto used in an exemplary embodiment of the method according to the invention;

FIG. 4 illustrates a side view of a virtual resection of a three-dimensional representation of the target bone of FIG. 3;

FIG. 5 illustrates a diagram of a database including a plurality of possible donor bones used in one exemplary embodiment of the method according to the invention;

FIG. 6 illustrates a side view of an actual resection of the target bone according to the virtual resection of FIG. 4;

FIG. 10 illustrates a side view of a virtual resection of the target bone of FIG. 3 including a proximal configuration of at least two proximal bore holes;

FIG. 11 illustrates a lateral view of a bone plate used in an exemplary embodiment of the method according to the invention;

FIG. 12 illustrates a side view of an implant or graft portion used in an exemplary embodiment of the method according to the invention;

FIG. 13 illustrates a side view of the remaining target bone with the inserted implant or graft portion of FIG. 8;

FIG. 14 illustrates a side view of a saw guide according to an exemplary embodiment of the system according to the invention;

DETAILED DESCRIPTION

Figure 1:
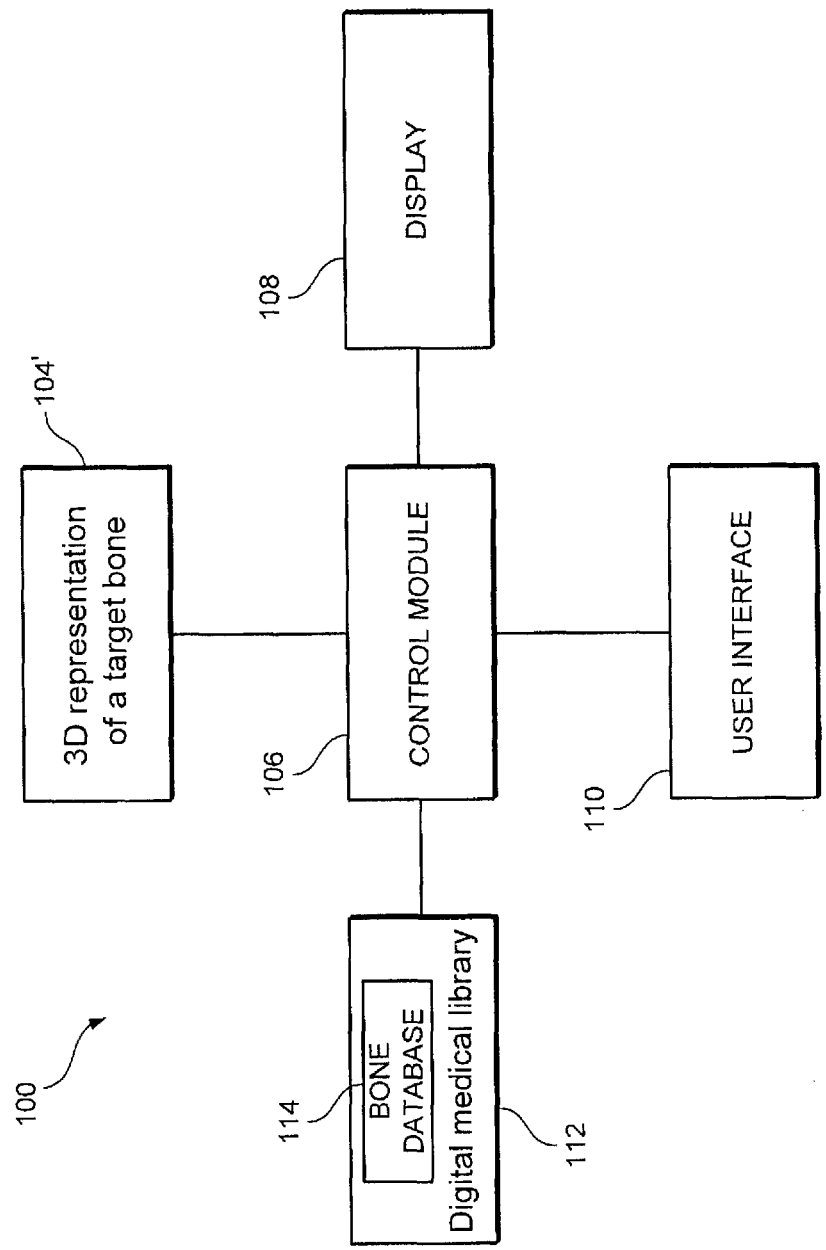
FIG. 1 illustrates a schematic view of an exemplary embodiment of a system according to the present invention.

The present invention may be further understood with reference to the following description and the appended drawings, wherein like elements are referred to with the same reference numerals. The present invention relates to the treatment of fractures including the use of markers in implant or bone graft procedures. Exemplary embodiments of the invention describe the use of one or more bone markers to accurately perform a virtual resection permitting an optimally suited replacement portion of bone to be selected, sized and shaped for precise fit with the edges of the cavity left by the resected portion of bone. It will be understood by those of skill in the art that, although the description and drawings specifically describe a resection and grafting procedure replacing a portion of a femur, this is exemplary only and the present invention may be applied to the application of an implant or bone graft to any bone within the body.

FIGS. 1-8 illustrate an exemplary embodiment of the system 100 for replacing a portion of a target bone 104 in a living body. As shown in FIG. 1, the system 100 may comprise a control module 106 processing data and/or user instructions entered via a user interface 110 and a display 108. The system 100 images the target bone 104 to produce a three-dimensional representation of the target bone 104', which may be displayed on the display 108. One or more markers 102 may be placed on the target bone 104 to establish a first reference system of coordinates 150 relative to a damaged portion of the target bone 104. Thus, the three dimensional representation of the target bone 104' also includes a three-dimensional first reference system of coordinates 150' defined by one or more first markers 102 attached to the target bone 104. The system 100 may also comprise a digital medical library 112 in the form of a set of digital data stored on a digital data carrier and comprising a bone database 114 with a plurality of potential suitable bones. The three-dimensional representation of the target bone 104' may be processed via the control module 106 and a three-dimensional representation of each of the potential suitable bones comprised in the digital medical library 112 can be imported into the control module 106 and processed during a surgical planning procedure.

Figure 2:
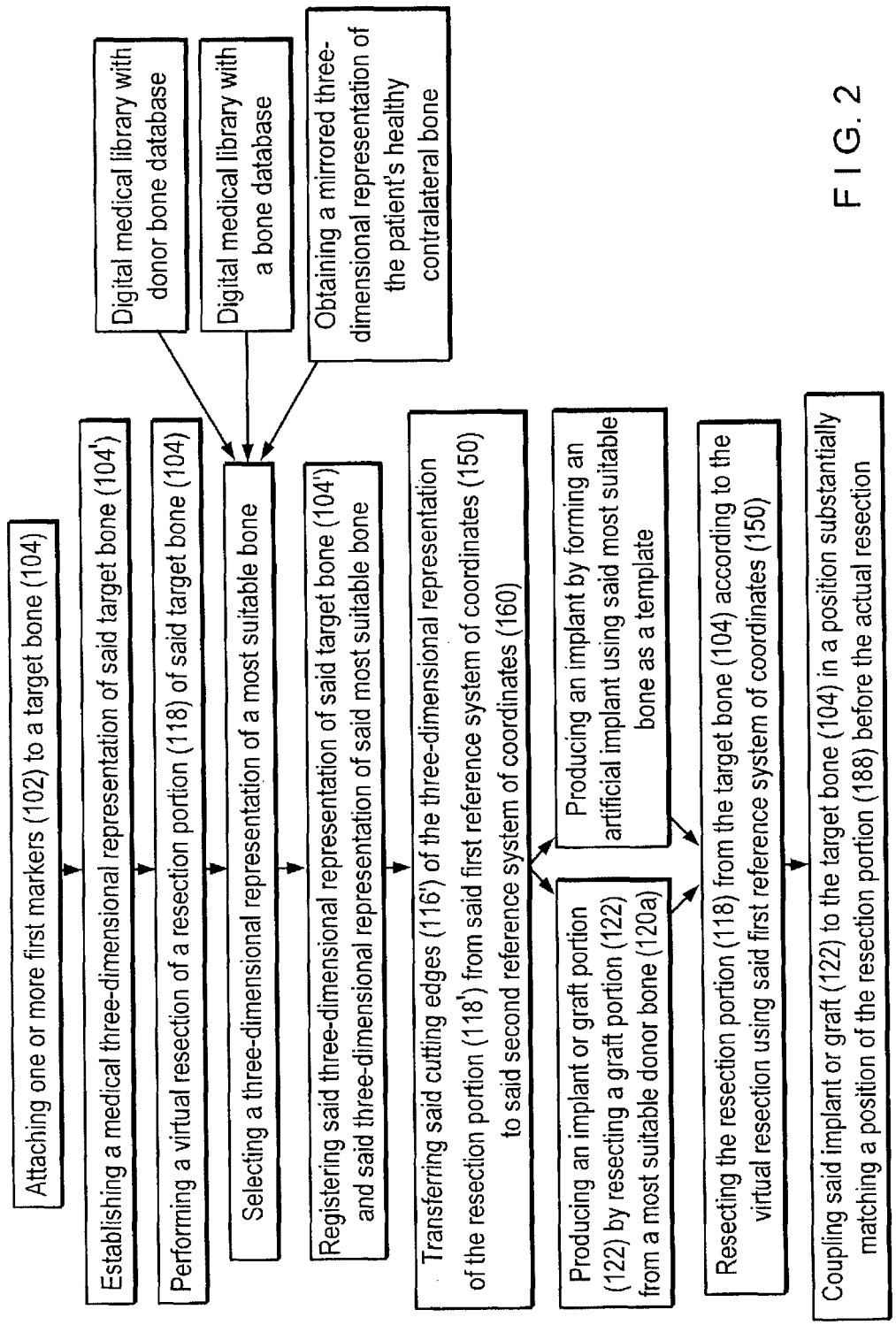
FIG. 2 illustrates a flow chart of several exemplary embodiments of the method according to the invention.

FIG. 2 illustrates the steps to be performed in a variety of embodiments of a method for replacing a portion of a target bone 104 in a living body according to the invention. The steps to be performed may include attaching one or more first markers 102 to the target bone 104 in a desired position relative to a resection portion 118 of the target bone 104 to be replaced. The one or more first markers 102 establish a three-dimensional first reference system of coordinates 150. A medical three-dimensional representation of the target bone 104' is established by using an X-ray device, computed tomography or magnetic resonance imaging. A virtual resection of a resection portion 118' on the three-dimensional representation of the target bone 104' may be performed using the first reference system of coordinates 150' via the control module 106. The virtual resection constructs a three-dimensional representation of a remaining portion of target bone 128' including cutting edges 116'. A three-dimensional representation of a most suitable bone may then be selected. The three-dimensional representation of the most suitable bone should most closely match the three-dimensional representation of the target bone 104' and either comprises one or more second markers 124', which define a three-dimensional second reference system of coordinates 160', or the one or more second markers 124 are virtually positioned in the selected three-dimensional representation of the most suitable bone.

The most suitable bone may be selected in any of a variety of different ways. For example, the selection may be performed by selecting a most suitable donor bone 120a from a plurality of donor bones 120 included in a bone database 114 in the form of a digital medical library 112. In another embodiment, a most suitable virtual bone may be selected from a bone database 114 in the form of a digital medical library 112, which may be used to provide a model for constructing an implant to replace a resected portion of the target bone 104. Alternatively, a three-dimensional representation of the patient's contralateral bone may be obtained and mirrored. The three-dimensional representation of the target bone 104' and the three-dimensional representation of the most suitable bone 500 are then registered and the cutting edges 116' of the three-dimensional representation of the remaining target bone 128' are transferred from the first reference system of coordinates 150' to the second reference system of coordinates 160'. An implant or graft portion 122 for replacing the resection portion 118 of the target bone 104 may be obtained by using the three-dimensional representation of the most suitable bone and the cutting edges 126' transferred to the second reference system of coordinates 160.

The implant or graft portion 122 may be obtained by resecting a graft portion 122 from a most suitable donor bone 120a by using the cutting edges 126' transferred to the second reference system of coordinates 160 defined by the one or more second markers 124. In another embodiment, the implant or graft portion 122 may be obtained by manufacturing an implant 126 using the three-dimensional representation of the most suitable virtual bone as a pattern. The resection portion 118 of the target bone 104 may then be resected according to the virtual resection using the first reference system of coordinates 150 and the implant or graft portion 122 coupled to the target bone 104 in a position substantially matching a position of the resection portion 118 before the actual resection.

As shown in FIGS. 3-8, an embodiment of the method according to the present invention comprises the use of at least one first marker 102 that is attachable to the target bone 104 and detectable by an X-ray device or other known surgical navigation device. If only one first marker 102 is used, the first marker 102 may have a shape, e.g. an L-shape, which allows a position of the first marker 102 to be detected with respect to six degrees of freedom. The exemplary procedure illustrated in FIG. 3 shows the first marker 102 attached to a target bone 104 such that a damaged portion of the bone 104 may be resected and fitted with a suitable bone graft or implant. More specifically in this example, the target bone 104 is a femur including a fractured/damaged lower extremity proximate a knee joint, which will be treated by attaching a bone graft thereto. The first marker 102 may be attached to the lower extremity of the target bone 104 (e.g., femur) within the damaged portion thereof to establish a three-dimensional first reference system of coordinates 150 relative to the portion of bone to be replaced by the graft. It will be understood by those of skill in the art, however, that the marker 102 may be attached to any portion of the target bone 104 so long as a position and/or orientation of the marker 102 is detectable relative to the target bone 104 and, in particular, to the damaged portion thereof to be replaced by the bone graft. The marker 102 may be attached to the target bone 104 via any attachment mechanism such as, for example, pins, nails, barbs, threads, screws, adhesive etc. The marker 102 may be inserted into the body and attached to the target bone 104 through a small incision such as, for example, a stab incision, an injection or an open incision.

The control module 106 may detect the position and/or orientation of the first marker 102 to provide the fixed reference system of coordinates 150' when an image of the three-dimensional representation of the target bone 104' is displayed on a display 108. The three-dimensional representation of the target bone 104' may be obtained from, for example, at least two x-ray images obtained at an angle relative to each other, a CT, a MRI, etc. Those skilled in the art will understand that the first marker 102 may be selected to ensure it is sufficiently visible and otherwise compatible in conjunction with the imaging apparatus to be employed. Images of the target bone 104 will then show the target portion of the target bone 104 and the precise location of the first marker 102 attached thereto. As would be understood by those skilled in the art, the control module 106 is then operated to perform a virtual resection of the three-dimensional representation of target bone 104', as shown in FIG. 4, with edges 116' of a virtually resected (e.g., damaged) portion 118' indicating guide planes or other surfaces along which the target bone 104 may be cut to perform an actual resection of the resection portion 118. The procedure of a virtual resection is known from preoperative planning of surgeries, like joint replacement or dental implantology.

Based on a 3D CT or MRI scan, the surgeon may define, for example, the location and size of a tumor or necrotic bone segment. The surgeon may import the three-dimensional representation of the target bone 104' into a preoperative planning software. This software allows the surgeon to visualize the damaged bone segment, take measurements and allows plan a bone resection by defining cutting lines and/or drill holes. This type of planning may be used to plan an intervention in some medical situations, but in the operating room, this type of planning may be used to plan a course of treatment for the patient. Due to the one or more first markers 102, a link is created between the bone/joint of the preoperatively planned intervention and the bone/joint of the patient in the operation room. In particular, the first markers 102 ensure that the three-dimensional representation of the target bone 104', and the virtual resections performed thereon, corresponds to the actual target bone 104 of the patient. Every planned bone cut, drill hole or implant position is referenced to the one or more first markers 102. If only one first marker 102 is used, it is preferred that this marker 102 have a shape, e.g. an L-shape, such that the first marker 102 is with respect to all degrees of freedom. It will be understood by those of skill in the art, however, that simpler markers maybe used, but will result in less detection of degree of freedom and may require more than one first marker 102 to be used. During surgery, the first marker 102 will be detected and the three-dimensional representation of the target bone 104' is displayed as an image on the display 108. An additional marker may also be attached to a surgical instrument such as, for example, an oscillating saw, which permits visualization of the location of the saw or other surgical instrument with respect to the target bone 104. Thus, the three-dimensional representation of the target bone 104' and the surgical instrument illustrates where the saw should make the cut, based on the preoperative planned procedure. The selection of the most suitable, respectively the best fitting donor bone 120a is done by using registration, i.e. 3D shape matching comparing the 3D bone shape of the target bone 104, with a selection of donor bones 120. One or more second markers 124 placed into the donor bones 120, allow to shape the selected most suitable donor bone 120a according to the needed shape, planned at the target bone 104.

Using the accurately known position of the first marker 102, the control module 106 locates the edges 116 of the resected portion 118 based on user input as to the desired location of the resection portion 118. As would be understood by those skilled in the art, a user may provide the data defining the desired characteristics of the resection portion 118 to the control module 106 via a user interface 110. For example, the user interface 110 may be a touch-screen display or a keypad and/or mouse such that the user may indicate the resection portion 118 of the target bone 104 to be resected (e.g., the damaged portion of the bone). Alternatively, the control module 106 may detect the fracture in the target bone 104 and automatically suggest the location of a virtual resection.

After the virtual resection has been performed, the user may further review a plurality of available donor bones 120 and may select several potentially suitable bones 120 for further analysis. As shown in FIG. 5, each of these potentially suitable bones 120 has been previously fitted with a second marker 124 and can be virtually resected in the same manner described above to determine which of these potentially suitable bones 120 includes a portion that is most suitable for grafting to the target bone 104. A portion corresponding to the resection portion 118 is virtually resected from each of the bones 120 and compared to the portion of the target bone 104 which will remain after the resection portion 118 is resected to determine which of these bones 120 will provide the most compatible graft, e.g. the graft which most closely matches the contours of the adjacent portions of the target bone 104. Once the most suitable virtual bone 120a has been identified, the actual resection of the graft portion 122 may be performed using the second marker 124 for guidance to ensure the actual resection accurately matches the virtual resection. Similarly to the actual resection of the target bone 104, during the actual resection of the graft portion 122, the display 108 may show, in real-time, images of the most suitable donor bone 120a to ensure that the actual resection corresponds to the virtual resection thereof.

Once a most suitable donor bone 120a has been selected from the bone database 114 and the graft portion 122 has been severed therefrom, the actual resection of the target bone 104 is performed based on the virtual resection of the target bone 104, as shown in FIG. 6. Specifically, the actual resection of the target bone 104 is performed relative to the position and/or orientation of the first marker 102 in the same position determined in the virtual resection. Those skilled in the art will understand that the first marker 102 may function during the actual resection in the same manner as in the virtual resection—i.e. defining a three-dimensional first reference system of coordinates 150 fixed on the target bone 104 used to locate other sites on the target bone 104 such as the edges 116 along which the resection portion 118 is to be resected. This facilitates the performance of the actual resection and enhances the accuracy of this procedure relative to the virtual resection so that a remaining portion 128 of the target bone 104 corresponds to the contours to which the graft was matched. During the actual resection, real-time images of the target bone 104 may be displayed on a display 108 to ensure that the actual resection corresponds to the virtual resection. For example, the actual cuts along the target bone 104 may be overlayed with the paths representing the virtual cuts from the virtual resection. As described above, an additional marker may also be placed in the cutting instrument such that a position of the cutting instrument relative to the target bone 104, may also be visualized in real time on the display 108 during the resection.

Figure 8:
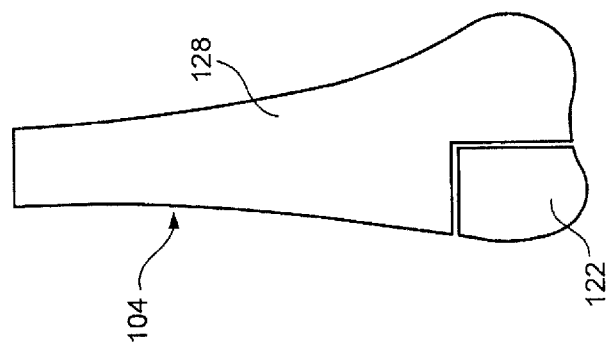
FIG. 8 illustrates a side view of an implantation of the graft portion of FIG. 7 fit with a remaining portion of the target bone of FIG. 6.
Figure 7:
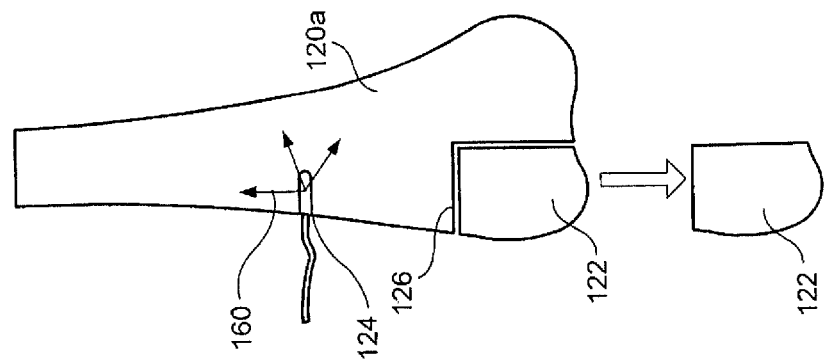
FIG. 7 illustrates a side view of a resection of a graft portion of a selected bone of the possible donor bones of FIG. 5.

When the actual resection of the target bone 104 has been completed, the graft portion 122 is placed into the space left by the resection of the resection portion 118 and, as shown in FIG. 8, the shape of the graft portion 122 may be adjusted to precisely match the edges 116 and/or dimensions of the resected portion 118 of the target bone 104 such that the graft portion 122 is a precise-fit with the target bone 104 as would be understood by those of skill in the art.

In an alternate embodiment, instead of the graft portion 122, an implant 126 may be manufactured of a biocompatible material via, for example, molding material to include edges and/or curvatures corresponding to the dimensions of the virtually resected portion 118. The implant 126 may, for example, be manufactured based on three dimensional representations of bones included in the bone database 114. Alternatively, the implant 126 may be formed using the dimensions of the resected portion 118 of the target bone 104. The design of such an implant 126 may be configured to encourage or discourage bone ingrowth as desired in any known manner.

The system 100 comprises or is connectable to a digital medical library 112 including a bone database 114 including images of suitable. The images of the suitable bones 120 may be shown on the display 108, as shown in FIG. 5. These images of suitable bones may, for example, be obtained via x-rays, CT scans, MRI or any other suitable imaging technology. These suitable bones 120 may be three dimensional representations of existing donor bones and/or virtual (e.g., model bones) that may be used to manufacture implants for grafting. The user may browse through the bone database 114 to find a most suitable bone 120a including a portion closely matching the virtually resected portion of the target bone 104. For example, the user may search for a suitable femur including a lower extremity with curvatures and/or edges most closely matching those of the resected portion 118—i.e., a bone which, if resected would provide a graft portion most smoothly meshing with the portion of the target bone 104 remaining after the resection portion 118 has been resected. Alternatively, the control module 106 may analyze the virtually resected portion 118 of the target bone 104, including curvatures, dimensions and measurements of the edges 116, and scan through the bone database 114, to locate one or more suggested suitable bones.

As shown in FIGS. 9-14, a method according to a further embodiment of the present invention, a bone plate 130 may be used to fix the graft 122 or the implant 126 to the remaining portion 128 of the target bone 104. A bone plate 130, as shown in FIG. 11, may have a proximal portion 11 including at least two plate holes 51, 52 via which the plate 130 may be fixed to the remaining target bone 128 and a distal portion 12 including at least two plate holes 53, 54 via which the plate 130 may be fixed to the implant 126. A three-dimensional representation of the bone plate 130 may be positioned in a desired position on the three-dimensional representation of the target bone 104', as shown in FIG. 10, during the surgical planning procedure. The proximal configuration 11' of at least two proximal bore holes 1', 2' may be virtually positioned in the three-dimensional representation of the remaining target bone 128' during the surgical planning procedure. The distal configuration 12 of at least two distal bore holes 3, 4 may also be virtually positioned in the three-dimensional representation of the implant 126.

At least two proximal bore holes 1, 2 of the proximal configuration 11 may then be drilled into the remaining target bone 128 in positions coinciding with the positions of the virtually positioned proximal configuration 11' of the at least two proximal bore holes 1', 2' by using the first reference system of coordinates 150 defined by the one or more first markers 102 as a reference. The at least two distal bore holes 3, 4 of the distal configuration 12 may be produced during manufacturing of the implant 126 by using the second reference system of coordinates 160. The implant 126 may be attached to the bone plate 130 by, for example, inserting bone fixation elements 132 through the at least two distal plate holes 53, 54 into the at least two distal bore holes 3, 4 in the implant 126 and aligning the implant 126 to the remaining target bone 128 by inserting bone fixation elements 132 through the at least two proximal plate holes 51, 52 into the at least two proximal bore holes (1, 2) in the remaining target bone 128, as shown in FIG. 9.

Further, as illustrated in FIG. 14 the system 100 may also comprise a saw guide 300 including a fixation portion 305 with a proximal configuration 11 of at least two fixation holes 301, 302 identical to the virtually positioned proximal configuration 11' and a guide portion including guiding means for a surgical saw along the cutting edges 116 defined during the surgical planning procedure.

Figure 9:
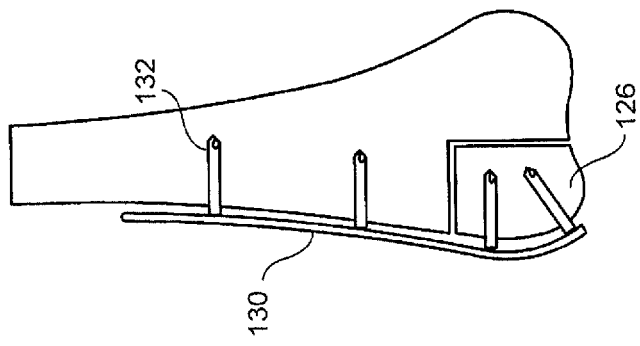
FIG. 9 illustrates a side view of a fixation of the inserted implant according to another exemplary embodiment of the invention.

As shown in FIG. 9, the implant 126 is fixed to the remaining portion 128 of the target bone 104 via implants such as, for example, the bone plate 130 and a plurality of bone fixation elements 132. The bone plate 130 joins the implant 126 with the remaining portion 128 of the target bone 104, facilitating bone growth between the remaining portion 128 of the target bone 104 and the implant 126 fixed thereto. It will be understood by those of skill in the art, however, that the implant 126 may be fixed to the remaining portion 128 of the target bone 104 via any known fixation method and/or device known in the art.

In a further embodiment, as shown in FIGS. 15-18, a system 200 according to a further embodiment of the invention is substantially similar to the system 100 described above, except that it includes a custom implant 230 to fix a graft portion 222 obtained in the same manner described above to a remaining portion 228 of a target bone 204 after resection of a resection portion 218 of the target bone 204 in the same manner described above. Specifically, the first marker 202 is attached to the target bone 204 in the same manner described above to enable the accurate location of the target positions on the target bone 204 to perform the virtual and actual resections of the resection portion 218. Specifically, a virtual resection of the target bone 204 relative to the first marker 202 is performed in the same manner indicated above by identifying edges 216 along which the target bone 204 should be cut to resect the resection portion 218 of the target bone 204. A graft portion 222 closely matching the remaining portion 228 is then selected in the same manner described above and resected from a donor bone 220 or formed from a suitable material as described above. Final adjustments to the size and shape of the graft portion 222 are then made to ensure a precise fit between the graft portion 222 and the remaining portion 228 of the bone.

Figure 16:
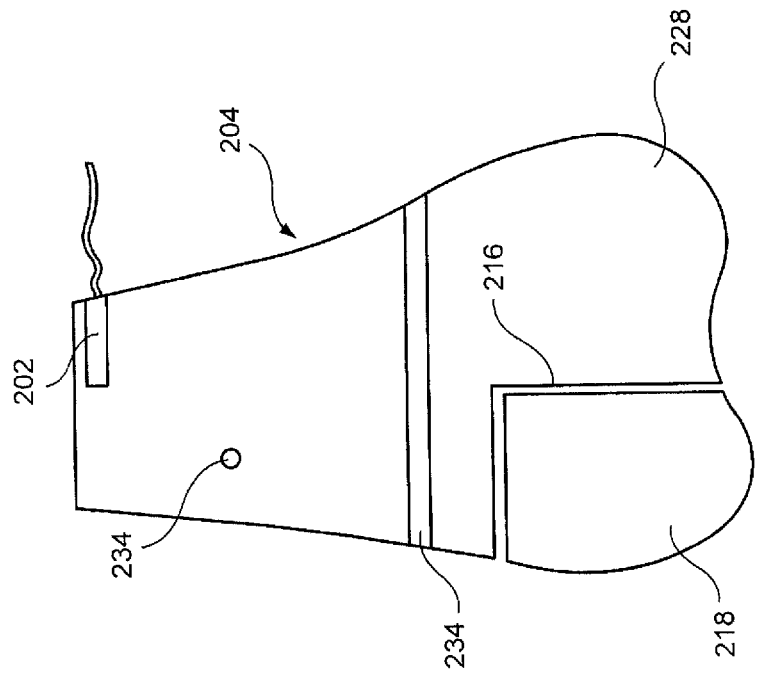
FIG. 16 illustrates a side view of a resected bone including drilled holes through a portion thereof.
Figure 15:
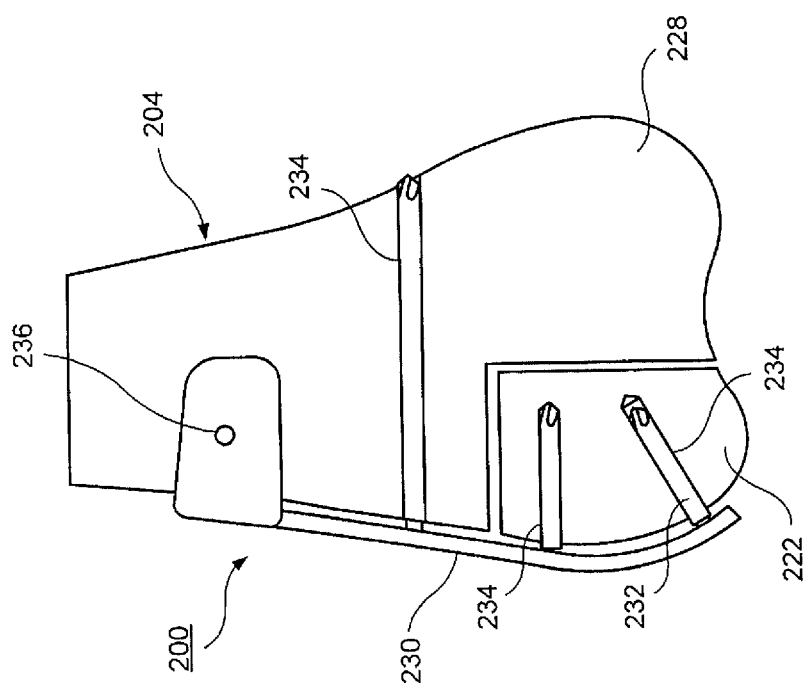
FIG. 15 illustrates a side view of a second exemplary embodiment of the present invention.
Figure 18:
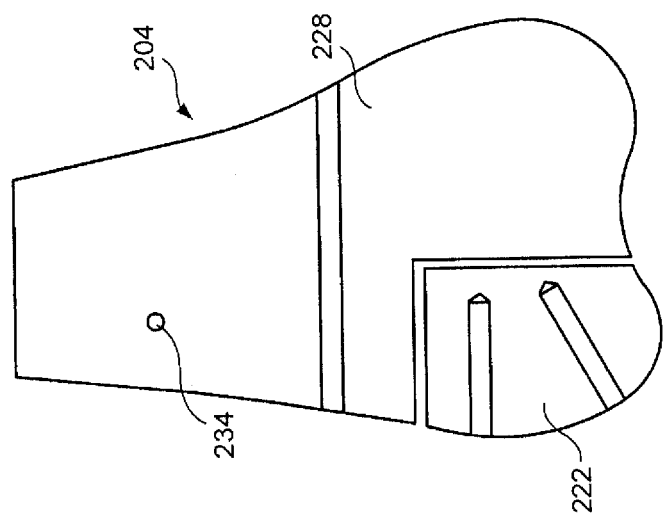
FIG. 18 illustrates a side view of the resected bone of FIG. 16 and the graft portion of FIG. 17.
Figure 17:
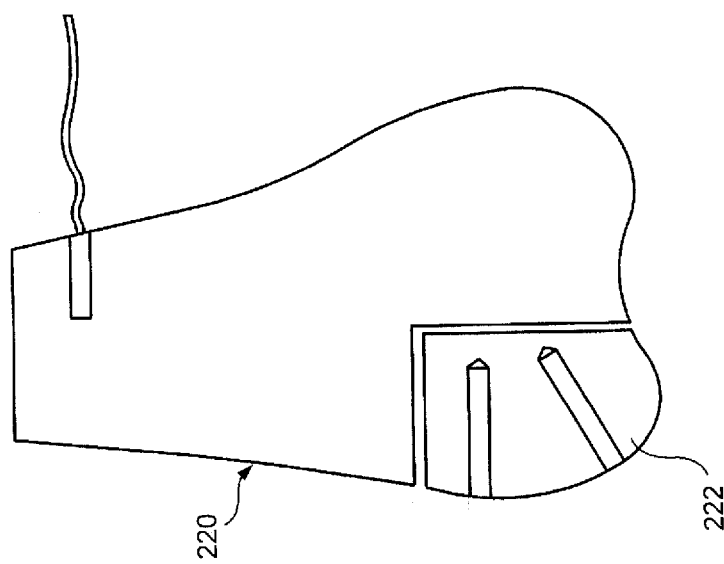
FIG. 17 illustrates a side view of a graft portion including drilled holes through a portion thereof.

Holes 234 are then drilled into the target bone 204 at positions corresponding to the target positions of openings in the custom implant 230—i.e., positions which will be aligned with the openings when the implant 230 is placed in a target position over the target bone 204 and the graft portion 222. Once again, the first marker 204 may be used to more accurately determine the target positions of the openings in the implant 230. As shown in FIGS. 16 and 17, the holes 234 may be drilled through either or both of the remaining portion 228 of the target bone 204 and the graft portion 222 as required to securely mount the implant 230 to the target bone 204 and to secure the graft portion 222 thereto. Then, when the graft portion 222 has been fitted with the remaining portion 228 of the target bone 204, as shown in FIG. 18, each of the holes 234 should correspond to a position and orientation of a corresponding one of the openings 236 of the implant 230 so that bone fixation elements 232 may be inserted therethrough into the target bone 204 or the graft portion 222, fixing the implant 230 to the target bone 204 and the graft portion 222 and securing the graft portion 222 to the target bone 204 in the desired orientation.

Although the invention and its advantages have been described in detail, it should be understood that various changes, substitutions, and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present invention.

It will be appreciated by those skilled in the art that various modifications and alterations of the invention can be made without departing from the broad scope of the appended claims. Some of these have been discussed above and others will be apparent to those skilled in the art.

What is claimed is:

1. A system for replacing a portion of a target bone in a living body comprising:
   a display displaying three-dimensional representation of the target bone including a three-dimensional first reference system of coordinates defined by a first marker attached to the target bone, the three-dimensional representation of the target bone defining a resection portion of the target bone to be resected therefrom; and
   a control module processing the three-dimensional representation of the target bone and based on input received via a user interface, to compare the three-dimensional representation of the target bone with reference data including three-dimensional representations of a plurality of virtual bones for the selection of one of a selected implant and graft portion suitable to replace the resection portion.

2. The system according to claim 1, further comprising a saw guide including a fixation portion with a proximal configuration including a plurality of fixation holes and a guide portion including guiding means for a surgical saw along predefined cutting edges.

3. The system according to claim 1, further comprising a bone plate including a proximal portion including a plurality of proximal plate holes, the proximal portion being configured for fixation to a remaining portion of the target bone after resection of the resection portion, and a distal portion including a plurality of distal plate holes, the distal portion being configured for fixation to the selected one of an implant and a graft portion.

4. The system of claim 3, wherein the control module virtually positions a three dimensional representation of the bone plate in a desired position on the three-dimensional representation of the target bone.

5. The system of claim 4, wherein the control module virtually positions the proximal configuration of at least two proximal bore holes in the three-dimensional representation of the remaining target bone.

6. The system of claim 4, wherein the control module virtually positions the distal configuration of at least two distal bore holes in the three-dimensional representation of the selected one of an implant and a graft.

7. The system according to claim 1, wherein the control module defines the resection portion of the target bone by obtaining a mirrored three-dimensional representation of the patient's contralateral bone wherein the three-dimensional representation of the patient's contralateral bone comprises one of a previously attached second marker defining a three-dimensional second reference system of coordinates and the second marker being virtually positioned in the three-dimensional representation of the patient's contralateral bone, registering the mirrored three-dimensional representation of the healthy contralateral bone and the three-dimensional representation of the most suitable virtual bone, and transferring the cutting edges at the three-dimensional representation of the remaining target bone from the first reference system of coordinates to the second reference system of coordinates.

8. The system of claim 1, wherein the control module selects a three-dimensional representation of a most suitable virtual bone from a plurality of virtual bones provided in a digital medical library, the three-dimensional representation of the most suitable virtual bone most closely matching the three-dimensional representation of the target bone and wherein the three-dimensional representation of the most suitable virtual bone one of the second marker defining a three-dimensional second reference system of coordinates and a second marker virtually positioned in the selected three-dimensional representation of the most suitable virtual bone, and wherein the control module registers the three-dimensional representation of the target bone and the three-dimensional representation of the most suitable virtual bone and transfers the cutting edges at the three-dimensional representation of the remaining target bone from the first reference system of coordinates to the second reference system of coordinates.

9. The system of claim 1, further comprising a digital medical library including a plurality of donor bone from which a three-dimensional representation of a most suitable donor bone to replace the resection portion is selected.

* * * * *

UNITED STATES PATENT AND TRADEMARK OFFICE
CERTIFICATE OF CORRECTION

PATENT NO.        : 9,161,821 B2
APPLICATION NO.   : 13/156703
DATED             : October 20, 2015
INVENTOR(S)       : Frigg It is certified that error appears in the above-identified patent and that said Letters Patent is hereby corrected as shown below:

In The Claims

Claim 1, Column 11, Line 42:
"a display displaying three-dimensional representation of" should read "a display displaying a three-dimensional representation of".

Claim 8, Column 12, Line 43:
"suitable virtual bone one of the second marker defining a" should read "suitable virtual bone comprises one of a second marker defining a".

Signed and Sealed this
Fifteenth Day of March, 2016

Michelle K. Lee
*Director of the United States Patent and Trademark Office*